(12) United States Patent
Joseph et al.

(10) Patent No.: US 8,809,400 B2
(45) Date of Patent: Aug. 19, 2014

(54) METHOD TO AMELIORATE OXIDATIVE STRESS AND IMPROVE WORKING MEMORY VIA PTEROSTILBENE ADMINISTRATION

(75) Inventors: James A. Joseph, Plymouth, MA (US); Agnes M. Rimando, Oxford, MS (US); Barbara Shukitt-Hale, Milford, MA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 114 days.

(21) Appl. No.: 13/204,891

(22) Filed: Aug. 8, 2011

(65) Prior Publication Data

US 2012/0035272 A1 Feb. 9, 2012

Related U.S. Application Data

(62) Division of application No. 12/136,341, filed on Jun. 10, 2008.

(60) Provisional application No. 60/970,591, filed on Sep. 7, 2007.

(51) Int. Cl.
*A61K 31/075* (2006.01)
*A61K 36/45* (2006.01)

(52) U.S. Cl.
USPC .......................................... 514/720; 424/732

(58) Field of Classification Search
None
See application file for complete search history.

(56) References Cited

U.S. PATENT DOCUMENTS

2005/0038125 A1* 2/2005 Smit et al. ..................... 514/720

OTHER PUBLICATIONS

Pari (Life Sciences (Jul. 2006), vol. 79, pp. 641-645).*
Joseph (Mechanisms of Ageing and Development (2000), vol. 116, pp. 141-153).*

* cited by examiner

*Primary Examiner* — Susan Hoffman
(74) *Attorney, Agent, or Firm* — John Fado; Albert Y. Tsui; Lesley Shaw`

(57) ABSTRACT

Disclosed is a pharmaceutical composition for treating oxidative stress comprising a therapeutically effective amount of a substantially pure compound of pterostilbene and a physiologically acceptable carrier. Pterostilbene is administered in an amount between about 2.5 mg to about 10 mg per kilogram of subject body weight. Also disclosed is a method for increasing a working memory of a subject, the method comprising administrating an effective amount of a substantially pure compound of pterostilbene, wherein the working memory for a subject increase and the therapeutic effectiveness is about 10 mg of pterostilbene per kilogram of subject body weight.

3 Claims, 7 Drawing Sheets

METHOD TO AMELIORATE OXIDATIVE STRESS AND IMPROVE WORKING MEMORY VIA PTEROSTILBENE ADMINISTRATION

CROSS-REFERENCE TO RELATED APPLICATION

This application claims the benefit of the filing date of the U.S. Provisional Patent Application Ser. No. 60/970,591 filed on Sep. 7, 2007.

The instant application is a Divisional of U.S. patent application Ser. No. 12/136,341 filed on Jun. 10, 2008.

FIELD OF THE INVENTION

This invention relates to a method for use of pterostilbene administered to a subject in an effective amount to forestall, prevent, and reverse the effects of neuronal and behavioral aging and development of neurodegenerative diseases. Specifically the resveratrol analog pterostilbene is effective in reversing motor deficits and working memory of subjects.

BACKGROUND OF INVENTION

Diet supplementation with fruits and vegetables has an impact of preventing and reversing defects associated with an aging subject. Nutritional regimes that involve dietary supplementations with berryfruit (e.g., *Vaccinium* berries such as cranberries and blueberries) reverse and/or forestall both motor and cognitive changes associated with aging. For example, blueberry supplementation prevents cognitive behavioral deficits in mice having increased amyloid β-peptide production with APP/PS-1 mutations. (Joseph J A. et al., 2003. *Nutr. Neurosci.*, 6: 153-162). The beneficial effects of berryfruits involve direct and indirect actions against oxidative stressors. As such, there is a need to identify compounds in berryfruit that are effective in altering oxidative mediated changes in motor and cognitive function.

Trans-3,5,4'-trihydroxystilbene (hereinafter referred to as resveratrol) has been identified as having a plurality of anti-aging properties due to its robust anti-oxidant activity. In vitro experiments have shown that resveratrol is an effective free radical scavenger and inhibits low density lipoprotein oxidation (Brito P. et al., 2002. *Free Radic Res.* 36 (6):621-631). Other stilbenoids such as pinostilbene, desoxyrhapontigenin, pterostilbene, resveratrol trimethylether, and piceatannol, have varying degree of biological activity and effectiveness for lowering lipid levels by activating a nuclear receptor, peroxisome proliferators activated receptor alpha isoform.

Trans-3,5-dimethoxy-4'-hydroxystilbene (hereinafter referred to as pterostilbene), a natural methylether analog of resveratrol, had been demonstrated to have antioxidant activity similar to that of resveratrol (Rimando et al., 2002. *J. Agric. Food Chem.* 50:3453-3457; Stivala et al., 2001. *J. Biol. Chem.* 276 (25):22586-22594.) Pterostilbene is present in some small fruits such as grapes (Adrian et al., 2000. *J. Argic. Food Chem.* 48:6103-6105) and berries of *Vaccinium* (*Vaccinium ashei* Reade and *Vaccinium stamineum* L.) (Rimando et al., 2004. *J. Argic. Food Chem.* 52:4713-4719) as well as in woody plants (Maurya et al., 1977. *J. Nat. Prod.* 47:179-181; Amone et al., 1977. *J. Chem. Soc. Perkins Trans.* 19:2116-2118). Additionally, a plurality of botanicals contain pterostilbene, including *Anogeissus acuminata, Dracaena cochinchinensis, Dracaena loureiri, Guibourtia tessmannii, Pterocarpus macrocarpus, Pterocarpus marsupium, Pterocarpus santalinus, Vaccinium ashei, Vaccinium corymbosum,* *Vaccinium deliciosum, Vaccinium membranaceum, Vaccinium ovatum, Vaccinium ovalifoilum, Vaccinium parviflorum, Vaccinium staminettm, Vaccinium uliginosum,* and *Vitis vinifrea*. Pterostilbene is also found in non-botanical sources such as propolis.

The level of pterostilbene can vary from species of *Vaccinium* berries. As reported by Rimando et al., 2004. *J. Argic. Food Chem.* 52:4713-4719, pterostilbene concentrations via cultivars of *Vaccinium* berries were reported having 99 ng/gm to 520 ng/gm of dry sample. Additionally, as reported by Rimando et al., *Acta Hort.* (ISHS). 680:137-143, lyophilized berries from *Vaccinium* nine cultivars species exhibited 0.12 μg to 2.74 μg of pterostilbene per gram of berries. Similarly, blueberry species vary in the amount of pterostilbene concentration. It has been reported that a range of 99 ng to 475 ng of pterostilbene can be derived from one gram of lyophilized blueberries.

Studies have linked the effects of antioxidants with deleterious effects of brain aging and behavior. The combination of antioxidant/anti-inflammatory polyphenolics found in fruits and vegetables in the form of "secondary chemicals" not generally involved in the plant primary metabolism, has exhibited efficacy in preventing these deleterious effects. As such, there is a need to further identify fruit and plants, specifically the compounds that can protect against aging and cognitive defects.

The compound pterostilbene has shown moderate inhibition of cyclooxygenase-1, and weak inhibition of cyclooxygenase-2 to suggest anti-inflammatory activity. (Rimando, et al., 2002. *J. Agric. Food Chem.* 50: 3453-3457.) In addition, pterostilbene has been identified to activate peroxisome proliferator-activated alpha isoform, (PPARα) a receptor proposed to mediate lowering lipid and glucose levels. Details of the PPARα agonist effect of pterostilbene is disclosed in Rimando et al., 2005. *J. Agric. Food Chem.* 53:3403-3407 and US2006/005723A1, both incorporated herein by reference.

Pterostilbene has been identified to inhibit colon carcinogenesis. Particularly, pterostilbene has suppressed azoxymethane-induced colonic aberrant crypt foci growth in weanling male F344 rats. Additionally, pterostilbene inhibits the expression of inducible nitric oxide synthase (iNOS) in HT-29 human adenocarcinoma cell lines. (Suh et al., 2007. *Clin Cancer Res.* 13 (1) 350-355.)

In an effort to ameliorate cognitive changes in senescent subjects, there is a need in the art to determine whether a supplementation of pterostilbene to senescent subjects would reverse cognitive and motor deficiencies as compared to unsupplemented subjects.

Muscarinic cholinergic receptors mediate the actions of the neurotransmitter acetylcholine in the central and peripheral nervous systems, gastrointestinal system, heart, endocrine glands, lungs, and other tissues. Five distinct muscarinic receptor subtypes have been identified as m1-m5. The m1 subtype is the predominant subtype found in the cerebral cortex and is believed to be involved in the control of cognitive functions.

Conditions associated with cognitive impairment, such as Alzheimer's disease, are accompanied by loss of acetylcholine in the brain. This is believed to be the result of degeneration of cholinergic neurons in the basal forebrain, which innervate areas of the association cortex, and hippocampus, which is involved in higher cognitive processes.

As such, there is a need to identify compounds that increase acetylcholine signaling effect in the brain. Specifically there is a need to identify compounds as muscarinic agonists that are active at various receptor subtypes in the central and peripheral nervous system.

BRIEF SUMMARY OF THE INVENTION

It is an object of this invention to provide a composition to treat the effects of neuronal and behavioral aging and prevent development of neurodegenerative diseases caused by oxidative stress.

Disclosed is a pharmaceutical composition for treating oxidative stress comprising a therapeutically effective amount of a substantially pure compound of the formula:

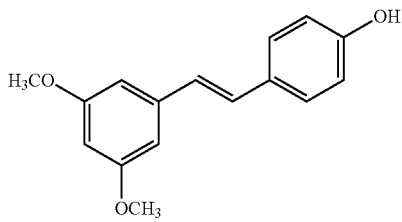 [SMILES: COc1cc(/C=C/c2ccc(O)cc2)cc(OC)c1]

and a physiologically acceptable carrier. In an embodiment of the invention, pterostilbene is administered in an amount between about 2.5 mg to about 10 mg per kilogram of subject body weight. In another embodiment of the invention, the therapeutic effective amount of pterostilbene is administered via a diet of *Vaccinium* berries. In another embodiment, the *Vaccinium* berries are blueberries.

Disclosed is a method for treating oxidative stress, the method comprising administering a therapeutically effective amount of a substantially pure compound of the formula:

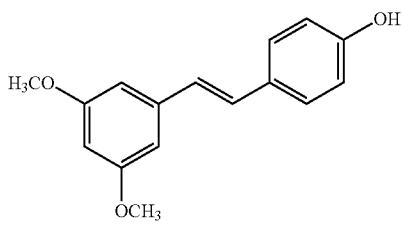 [SMILES: COc1cc(/C=C/c2ccc(O)cc2)cc(OC)c1]

wherein oxidative stress for the subject is reduced. In an embodiment of the invention, pterostilbene is administered in an amount comprising about 2.5 mg to about 10 mg per kilogram of subject body weight. In another embodiment, the compound increases subject acetylcholine receptor activity. Yet in another embodiment, the amount of compound administered protects against inhibition of dopamine release upon subjecting the subject to an oxidative stressor. In another embodiment, pterostilbene is administered via a diet of *Vaccinium* berries. In another embodiment, the *Vaccinium* berries are blueberries. In another embodiment, pterostilbene increases calcium buffering ability of muscarinic receptor subtypes, such as subtype is m-1. Also disclosed is a method for increasing the working memory of a subject, the method comprising administrating an effective amount of a substantially pure pterostilbene, wherein the working memory for a subject increases. In one embodiment, the therapeutic effective amount of pterostilbene is about 10 mg of compound per kilogram of subject body weight.

BRIEF DESCRIPTION OF THE DRAWING

The present invention together with the above and other objects and advantages may best be understood from the following detailed description of the embodiment of the invention illustrated in the drawings, wherein.

DETAILED DESCRIPTION OF THE INVENTION

Figure 1:
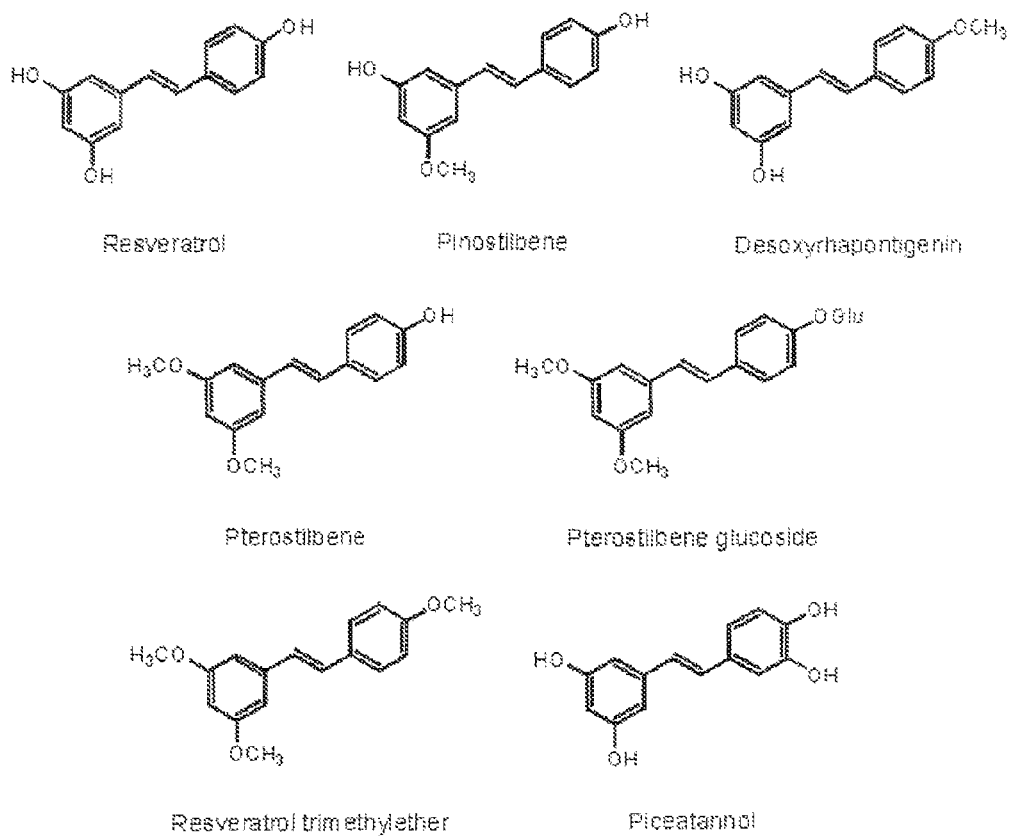
FIG. 1 depicts chemical structures of various stilbene derivatives.

Senescent subjects were administered a plurality of pterostilbene doses supplementing their diet. Pterostilbene-supplemented subjects exhibited improved psychomotor and cognitive performance as compared to those without pterostilbene supplementation. In another embodiment, subjects were administered with a low dose of pterostilbene at 2.5 mg of pterostilbene per kilogram of subject weight. In another embodiment, subjects were administered with a high dose of pterostilbene at 10 mg of pterostilbene per kilogram of subject weight and exhibited the greatest improved cognitive performance in tests assessing working memory. In another embodiment, pterostilbene pre-treatment antagonized the negative effect of dopamine treatment on calcium clearance following oxotremorine-induced depolarization in an M1-transfected COS-7 cell line. In yet another embodiment of the invention, a therapeutic amount of pterostilbene was administered wherein said cell lines transfected with oxidative stress sensitive muscarinic acetylcholine receptors protected against dopamine-induced decreases in recovery time. Furthermore, pterostilbene administered in subject diet increases the sensitivity of subject muscarinic receptors of post-mortem striatal slices wherein dopamine release does not decrease upon subjection to an oxidative stressor.

DEFINITIONS

As used in the specification and claims, the singular form "a", "an" and "the" include plural references unless the context clearly dictates otherwise. For example, the term "a cell" includes a plurality of cells, including mixtures thereof.

The term stilbene is used to describe a chemical class of compounds having the general formula of trans-1,2-diphenylethylene, having the molecular formula $C_6H_5CH=CHC_6H_5$. Stilbenes have the general structure of 1,2-diphenylethylene with two phenyl groups branching as side chains. One chemical derivate from the stilbene chemical class is resveratrol, which is trans-3,5,4'-trihydroxystilbene and depicted in FIG. 1. Another chemical derivative from the stilbene chemical class is pterostilbene, which can be described as trans-3,5-dimethoxy-4'-hydroxystilbene and depicted in FIG. 1. Other examples of stilbene include pinostilbene (trans-3,4'-dihydroxy-5-methoxystilbene), desoxyrhapontigenin (trans-3,5-dihydroxy-4'-methoxystilbene), pterostilbene glucoside, resveratrol trimethylether (trans-3,5,4'-trimethyletherstilbene), and piceatannol (trans-3,4,3',5'-tetrahydroxystilbene).

The term oxidative stressor refers to reactive oxygen species that react with various substances in the body causing disorders. Generally, hydroxyl radical indiscriminately reacts with a plurality of organic substrates. Examples of oxidizing stressor are hydrogen peroxide and ozone.

The term "working memory" as used herein refers to the fast memory process for storage and retrieval, including processes required to retain incoming information in short-term memory before it is converted to long-term memory, including the processes that support the retrieval of established long-term (episodic) memories. The term also refers to a short-term memory, primary memory, immediate memory, operant memory, and provisional memory.

A therapeutically effective amount is defined as an amount of a compound that, when administered to a subject, is sufficient to effect such treatment of a conditioned state. The "therapeutically effective amount" may vary depending on the compound, and condition being treated, the age and relative health of the subject, the route and form of administration, the judgment of the one having ordinary skill in the art, and other factors.

For each behavioral measure, between-subjects analysis of variance (ANOVA) models comparing the three groups were performed using Systat (SPSS, Inc., Chicago, Ill.) to test for statistical significance at the $p<0.05$ level. Days or trials, when appropriate, were included in the model as a within-subjects variable. Post-hoc comparisons, to determine differences among diet groups, were performed using Fisher's LSD post-hoc analysis.

A plurality of stilbene analogs were utilized in a calcium recovery assay in M1-transfected cell line following dopamine administration, those stilbene analogs are depicted in FIG. 1. Resveratrol was purchased from Sigma-Aldrich (St. Louis, Mo.) while piceatannol was purchased from Calbiochem-Novabiochem Corp. (San Diego, Calif.).

Pterostilbene (trans-3,5-dimethoxy-4'-hydroxystilbene) was synthesized (as modified from Pettit et al., 1988, *J. Nat. Prod.* 51:517-527) by condensation of 3,5-dimethoxybenzaldehyde and 4-hydroxyphenylacetic acid in acetic anhydride and triethylamine. The reaction mixture was heated (150° C.) under an atmosphere of nitrogen, and continuously stirred. After 20 hours, the reaction was stopped, cooled to room temperature, and concentrated hydrochloric acid (5 mL) was added. The formed precipitate was dissolved in 50 mL chloroform and extracted with 10% aqueous sodium hydroxide. The aqueous extract was acidified to pH 1 with concentrated hydrochloric acid, and stirred for at least 6 hours, resulting in the precipitation of the intermediate product, α-[(3,5-dimethoxyphenyl)methylene]-4-hydroxy-(αZ)-benzeneacetic acid. This intermediate product was heated with 1.0 g of copper in 10 mL quinoline (200° C., 6 hours, under nitrogen). The reaction mixture was cooled to room temperature and filtered. 5 N hydrochloric acid (25 mL) was added to filtrate, stirred for 1 hour, and extracted with chloroform. The chloroform extract containing impure pterostilbene was purified by flash chromatography on a Horizon HPFC system (Biotage, Inc., Charlottesville, Va.), using silica gel column, and solvent system ethyl acetate:hexane (linear gradient from 15:85 to 100% ethyl acetate). Fractions containing pure pterostilbene were combined and concentrated in vacuum. Pterostilbene was recrystallized in hexane, and its structure confirmed from its spectroscopic data (UV, mass spectrometry, and nuclear magnetic resonance spectroscopy).

Pterostilbene glucoside was synthesized via pterostilbene (20 mg) mixed with 40 mg of acetobromo-α,D-glucose (Sigma-Aldrich, St. Louis, Mo.) and potassium hydroxide (5 mg) in 1 mL of ethanol, and stirred for two days in room temperature. Pterostilbene glucoside was purified by preparative layer chromatography using methanol:chloroform as developing solvent (20:80). The structure of pterostilbene glucoside was determined by mass spectrometry and $^1$H-nuclear magnetic resonance spectroscopy.

A solution of resveratrol (150 mg in 3.0 ml of methanol) was treated with diazomethane, dropwise, and the methylation reaction was monitored by thin layer chromatography. Desoxyrhapontigenin, pinostilbene and resveratrol trimethylether were purified by preparative layer chromatography using hexane:ethyl acetate (8:2) as developing solvent. The retention factor values ($R_f$) for desoxyrhapontigenin, pinostilbene, and resveratrol were 0.2, 0.25, and 0.8, respectively). The structures of these compounds were confirmed by mass spectrometry and nuclear magnetic resonance spectroscopy.

Subject and Diet Preparation

Forty-two 19-month-old male Fischer 344 rats were obtained from the NIA colony (Harlan Sprague Dawley, Indianapolis, Ind.). The rats were individually housed in stainless steel mesh suspended cages, provided food and water ad libitum, and maintained on a 12-hour light/dark cycle. The rats were given one week to adjust to their new environment, after which time they were weight matched and then randomly placed on one of three diets for 12-13 weeks total (n=14/group): control, low dose pterostilbene (0.004%, equivalent to 2.5 mg/kg body weight), or high dose pterostilbene (0.016%, equivalent to 10 mg/kg body weight). All animals were observed daily for clinical signs of disease.

The pterostilbene diets were prepared at Harlan Teklad (Madison, Wis.) by adding crystalline pterostilbene to the control diet, of 40 mg/kg diet, 0.004% w/w for low dose, 160 mg/kg diet, 0.016% w/w for high dose. See Table 1 for diet composition. The amount of corn in the control diet was adjusted to compensate for the added volume of the pterostilbene. The rats were maintained on either the control or pterostilbene diet for eight weeks before motor testing and nine weeks before cognitive testing at 21 months.

TABLE 1

| Basal mix | g/Kg |
|---|---|
| Wheat, Hard, ground | 362.75 |
| Corn, yellow, ground | 193.80 |
| Wheat Middlings | 102.00 |
| Oats, ground | 102.00 |
| Fish Meal, Menhaden, 60% | 91.80 |
| Soybean Meal, 48% | 51.00 |
| Alfalfa Meal, Dehydrated, 17% | 20.40 |
| Corn Gluten Meal, 60% | 20.40 |
| Dicalcium Phosphate, 18.5%, FG | 15.30 |
| Soybean Oil | 15.30 |
| Brewer's Yeast, Dried, FG | 10.20 |
| Salt, Iodized NaCl | 5.10 |
| Calcium Carbonate, 38%, FG | 4.85 |
| Vitamin Mix, NIH-31 (TD 87391) | 3.57 |
| Mineral Mix, NIH-31 (TD 76121) | 1.53 |

Control diet - 98% basal mix + 2% corn
Low dose pterostilbene diet - 98% basal mix + 1.996% corn (1.96 g/kg) + 0.004% (0.040 g/kg) crystalline pterostilbene
High dose pterostilbene diet - 98% basal mix + 1.984% corn (1.84 g/kg) + 0.016% (0.160 g/kg) crystalline pterostilbene The following non-limiting examples are provided to further illustrate various embodiments of the present invention.

Example 1

Cell Treatments Against Oxidative Stress

COS-7 cells, a cell line derived from African green monkey kidney, were grown in Dulbecco's Modified Eagle's Medium (D-MEM) supplemented with 10% fetal bovine serum (FBS) and containing 100 U/ml penicillin and 100 ug/ml streptomycin sulfate. Twenty four hours prior to transfection, cells were harvested with trypsin, counted, and plated on 100 mm$^2$ tissue culture plates at 5×10$^6$ cells/plate. Cells were transiently transfected with rat muscarinic receptor subtype 1 DNA by the DEAE-dextran method. After transfection, cells were incubated 2.5 hours in growth medium containing 80 µM chloroquine to minimize degradation of the DNA. Transfected cells were then maintained in growth medium for 48 hours, harvested with trypsin, plated to coverslips in 35 mm plates for calcium imaging, and incubated overnight.

Cell Treatments

Blueberry (BB) extract (2 mg/ml), stilbenes [resveratrol (50 µg/ml), pinostilbene (50 µg/ml), desoxyrhapontigenin (25 µg/ml), pterostilbene (10 µg/ml), pterostilbene glucoside (10 µg/ml), resveratrol trimethylether (10 µg/ml), piceatannol (10 µg/ml)] and dopamine (1 mM) treatments were carried out as described previously in Joseph J. et al., 2004. *J. Alz. Dis.* 6:403-411, and hereby incorporated by reference. The BB extract and stilbenes were dissolved in growth media and cells were subsequently incubated for 45 minutes at 37° C. with the treated growth medium, followed by dopamine administration for 4 hours. Following these incubations, the cells were washed three times with extract-free growth medium prior to testing.

Calcium imaging was carried out using a Medical Systems Corp. open perfusion micro-incubator (37° C.) with temperature control that was mounted on the stage of a Nikon Eclipse TE200U microscope and illuminated with a fluorescent light source. Transfected cells were loaded with Fura-2/acetoxymethyl ester (2 µM) in loading medium (99% DMEM 1% FBS) for 40 minutes at 37° C. with 5% CO.

Real time analyses of calcium flux prior to and following 750 µM oxotremorine-induced depolarization were then carried out using Simple PCI software (Compix, Inc. Mars, Pa.). Response and recovery were then determined for each sample. Response was determined by examining whether a cell showed increases in $[Ca^{2+}]_i$ to oxotremorine by >30% over baseline. Only those cells that showed this magnitude of response were considered for further analysis. Recovery was determined by assessing the time (within 300 sec) for the $Ca^{2+}$ levels to return to 20% of the increase following depolarization in the cells that responded. Data was analyzed by Kruskal-Wallis one-way analysis of variance and Mann-Whitney U tests.

Figure 2:
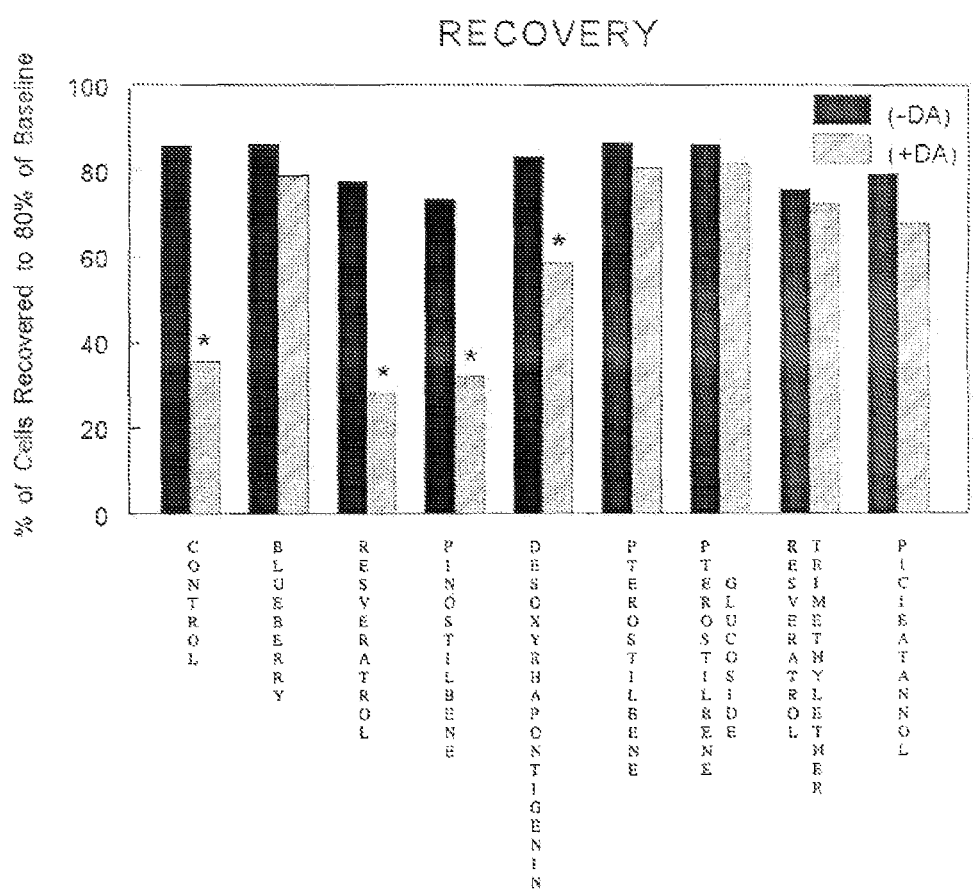
FIG. 2 is a graph Mean $Ca^{2+}$ Recovery in M1-transfected COS-7 cells control cells, and those pre-treated with blueberry, resveratrol, pinostilbene, desoxyrhapontigenin, pterostilbene, pterostilbene glucoside, resveratrol trimethylether, or piceatannol, following 0 dopamine (−dopamine) or 1 mM dopamine (+dopamine) treatment. The asterisk indicates a difference in recovery between non-dopamine-treated and dopamine-treated cells for each treatment (*=$p<0.001$)

Administration of dopamine significantly reduces recovery from an [80% baseline] in M1-transfected cells (control vs. dopamine-treated cells, p<0.001) (FIG. 2). Pterostilbene, pterostilbene glucoside, resveratrol trimethylether, and piceatannol protected against the dopamine-induced decreases in Recovery (p>0.05), while resveratrol, pinostilbene and desoxyrhapontigenin offered no protection (p<0.001) (FIG. 2).

Example 2

Morris Water Maze

The Morris Water Maze (MWM) is a method to test spatial learning and memory of subjects. Developed by Richard Morris, the MWM is an age and diet sensitive learning paradigm that requires a subject to locate a hidden platform (10 cm in diameter) positioned below the surface (2 cm) of a circular pool of water (134 cm in diameter×50 cm in height, maintained at 23° C.) based on distal cues, and to remember its location from the previous trial. Accurate navigation is rewarded with escape from the water onto the platform, for which the subject uses distal cues such as posters, the experimenter, a computer, cage racks, to effectively locate. The working memory version of the MWM (Brandeis et al., 1989. *Int J Neurosci.* 48:29-69; Morris R., 1984. *J Neurosci Methods.* 11: 47-60.) was performed daily for four consecutive days during the ninth week of treatment, with a morning and an afternoon session, two trials each session, with a 10 minute inter-trial interval between the two trials. Rats were tested in a random manner, with the restriction that one subject from each group be tested in succession. At the beginning of each trial, the subject was gently immersed in the water at one of four randomized start locations. Each subject was allowed 120 seconds to escape onto the platform; if the subject failed to escape within this time, it was guided to the platform. Once the subject reached the platform, it remained there for 15 sec (Trial 1; reference memory or acquisition trial). The subject was returned to its home cage between trials (10 min). Trial 2 (the working memory or retrieval trial) used the same platform location and start position as Trial 1. Performances were videotaped and analyzed with image tracking software (HVS Image, UK), which allows measurements of latency (sec) (time to find the platform), path length (cm), and swimming speed (cm/sec; latency/path length). A detailed description of the maze and the paradigm used is disclosed in Shukitt-Hale et al., 1998. *Experimental Gerontology,* 33:615-624, and incorporated herein by reference.

Figure 3:
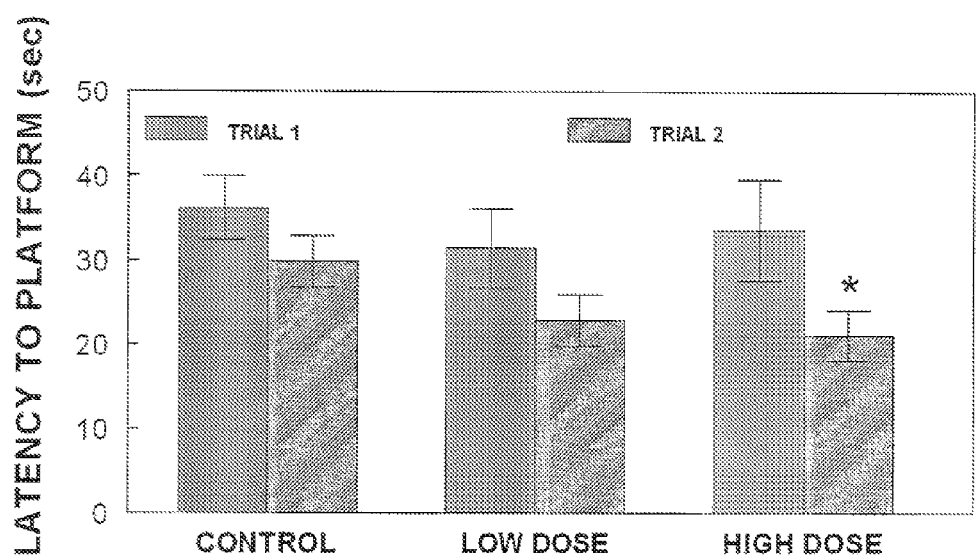
FIG. 3 is a graph of latency to platform measurement in seconds of subjects administered a low supplement of pterostilbene (0.004% w/w), a high supplement of pterostilbene (0.016% w/w), or no pterostilbene in their diet (control). The asterisk indicates a difference between Trial 1 and Trial 2 performance for each diet group (*=$p<0.05$)
Figure 4:
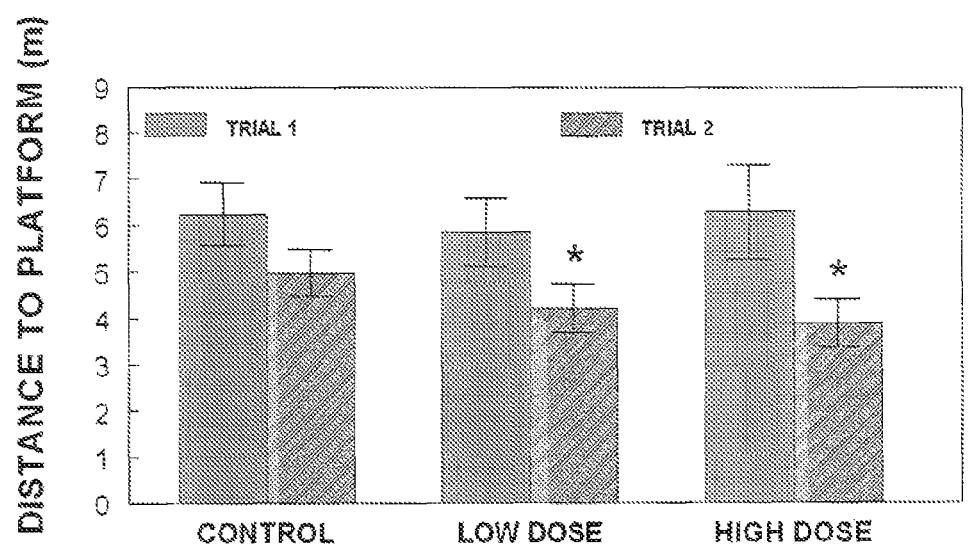
FIG. 4 is a graph of distance to platform measurement in meters for subjects administered a low supplement of pterostilbene (0.004% w/w), a high supplement of pterostilbene (0.016% w/w), or no pterostilbene in their diet (control). The asterisk indicates a difference between Trial 1 and Trial 2 performance for each diet group (*=$p<0.05$)

Rat subjects were administered with pterostilbene diet as detail supra exhibited improved spatial memory performance compared to the control diet fed group (FIGS. 3 and 4). There were no differences in latency or distance to find the platform for Trial 1 or Trial 2 between the diet groups. However, separate t-tests were performed between the two trial latencies or distances for each group for days 3 and 4 (the days which rely more on memory than learning) in order to determine if the different diet groups significantly improved their performance from Trial 1 to Trial 2, an indication of improved working memory. The high dose pterostilbene group showed a significant (p<0.05) difference in latency to find the platform between Trial 1 and Trial 2, i.e., Trial 2 latencies were significantly less than Trial 1, showing that these rats demonstrated one-trial learning, even with the 10 minute retention interval (FIG. 3). This one-trial learning was not found in the control group, while the low dose pterostilbene group tended to improve from Trial 1 to Trial 2 (p=0.09). Additionally, both the low and high dose pterostilbene groups showed significant (p<0.05) differences in distance to find the platform between Trial 1 and Trial 2, i.e., Trial 2 distances were significantly less than Trial 1 (FIG. 4). The control group did not show this improvement from Trial 1 to Trial 2 (p>0.05). Therefore, pterostilbene reversed the deleterious effects of aging on cognitive performance, particularly working memory, in a dose-dependent manner.

Pterostilbene In Subject Hippocampal Tissue

Hippocampal brain tissue was extracted from subjects that were euthanized 2-3 weeks following Morris Water Maze testing. The tissue samples were stored at $-80°$ C. and thawed in ice prior to extraction. Tissues were homogenized in 500 µL of phosphate buffer (pH 7.4) then centrifuged (7000 g, 4° C., 15 min). The supernatant was collected and homogenization was repeated. The combined supernatant was extracted with ethyl acetate (500 µL×2). The ethyl acetate extract was dried under a stream of nitrogen.

The dried extract was treated with 30 µL of N,O-bis[trimethylsilyl]trifluoroacetamide:dimethylformamide (BSTFA: DMF, 1:1; Pierce Biotechnology, Inc., Rockford, Ill.) and heated at 70° C. for 40 min. The derivatized sample was used for analysis of pterostilbene by gas chromatography-mass spectrometry (GC-MS). GC-MS was performed on a JEOL GCMate II Instrument (JEOL USA Inc., Peabody, Mass.) using a J&W DB-5 capillary column (0.25 mm internal diameter, 0.25 µm film thickness, 30 m length; Agilent Technologies, Foster City, Calif.). The GC was run under the following temperature program: initial 190° C., increased to 239° C. at 20° C./min rate and held at this temp for 3 min, increased to 242° C. at the rate of 0.2° C./min, then finally increased to 300° C. at the rate of 25° C./min and held at this temperature for 1.5 min. The carrier gas was ultrahigh purity helium, at 1 mL/min flow rate. The injection port, GC-MS interface and ionization chamber were at 250, 230 and 230° C., respectively. The volume of injection was 1 µL, splitless injection. Mass spectrum was acquired in positive, electron impact (70 eV), low-resolution mode. Pterostilbene was determined and quantified from a reconstructed ion chromatogram using m/z 328, 313, 297 and 147. Quantitation was performed from calibration curve of a standard sample of pterostilbene (retention time, 12.5 min). GC-MS analyses were performed in duplicates. Hippocampal pterostilbene was only detectable in the high dose pterostilbene group and was 1.352±0.465 ng/tissue sample.

Figure 6A:
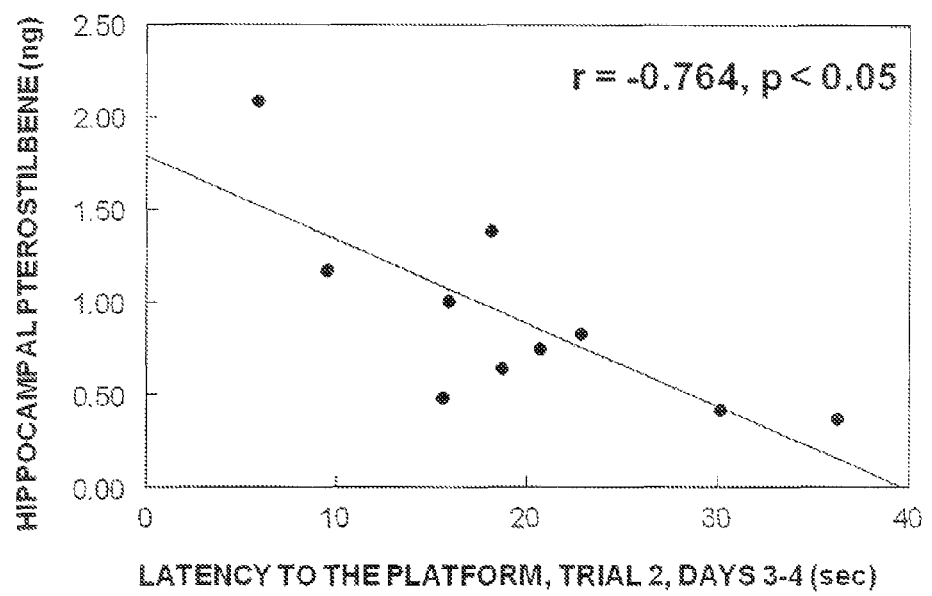
FIG. 6A is a graph depicting pterostilbene amount (ng) in the hippocampus of subjects as a function of latency in finding a platform (seconds) performed in a Morris Water Maze. Pterostilbene was measured in the hippocampus of subjects and correlated with the performance of subjects of Trial 2 from days 3 and 4.
Figure 6B:
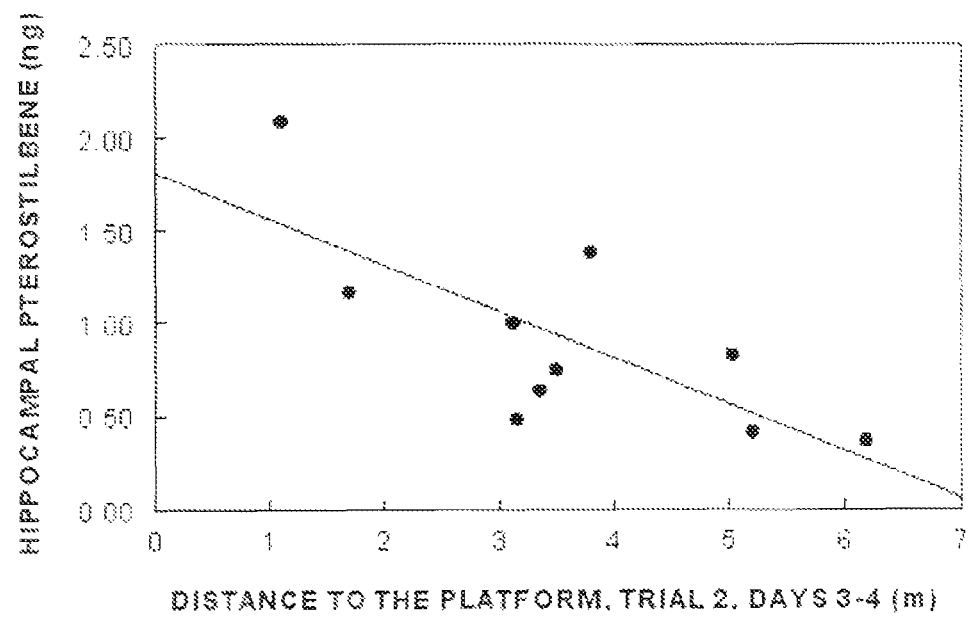
FIG. 6B is a graph depicting pterostilbene amount (ng) in the hippocampus of subjects as a function of distance (meters) traversed by a subject in reaching a platform performed in a Morris Water Maze. Pterostilbene was measured in the hippocampus of subjects of Trial 2 from days 3 and 4.

To examine whether there was a relationship between MWM behavior of the high dose pterostilbene rats and pterostilbene levels in the brain, hippocampal pterostilbene levels were correlated with Trial 1 and Trial 2 latency and distance performance as detailed in FIGS. 6A and 6B. The hippocampus is known for its role in spatial learning and memory, particularly Trial 2 working memory and found a significant negative correlation between hippocampal pterostilbene levels and Trial 2 performance on Days 3 and 4 for latency (r=−0.764, p=0.010) and distance (r=−0.734, p=0.016); i.e., as pterostilbene levels increased, the latency and distance to find the platform decreased.

Example 3

Dopamine Release

The muscarinic enhancement of $K^+$-evoked dopamine release ($K^+$-ERDA) from superfused striatal slices is an indicator of receptor sensitivity and striatal function and is sensitive to aging and oxidative stress as disclosed in Joseph et al., 1988. *Brain Res.*, 454:140-8; Joseph et al., 1988. *Brain Res.*, 454:149-55; Joseph J., et al., 1990. *Brain Res.*, 537:40-48; Joseph et al., 1996. *Free Radic. Biol. Med.*, 20: 821-30 and herein incorporated by reference. Additionally, muscarinic enhancement of dopamine release is sensitive to dietary supplementation as disclosed in Joseph et al., 1998. *J. Neurosci.*, 18: 8047-8055; Joseph et al., 1999. *J. Neurosci.*, 19: 8114-8121; Youdim et al., 2000. *Nutr Neurosci.*, 3: 383-97; Shukitt-Hale et al., 2005. *Age.*, 27: 49-57; Shukitt-Hale et al., 2006. *Nutrition*, 22: 295-302 and herein incorporated by reference. The protective capacity of the striatal tissue obtained from the control and supplemented groups were assessed by examining differences in the oxotremorine-enhancement of striatal $K^+$-ERDA. Dopamine release was conducted 2-3 weeks following behavioral testing on freshly dissected and cross cut (300 µm, McIlwain tissue chopper) striatal slices from subject brains that were fed a high dose, low dose and control diet. The slices were placed in small glass vials containing modified Krebs-Ringer basal release medium (BRM) that had been bubbled for 30 min with 95% $O_2$/5% $CO_2$ and containing 21 mM $NaHCO_3$, 3.4 mM glucose, 1.3 mM $NaH_2PO_4$, 1 mM EGTA, 0.93 mM $MgCl_2$, 127 mM NaCl and 2.5 mM KCl (low KCl) (pH 7.4). Half of the tissue was treated with 50 µM $H_2O_2$ to assess the effect of diet under conditions of oxidative stress. The slices were placed in the perfusion chambers and maintained at 37° C. and perfused with the BRM for 30 minutes. Following this equilibration period, the medium was switched to one containing (in mM) KCl 30 (high KCl), $CaCl_2.2H_2O$ 1.26 (in place of EGTA), NaCl 57, and 0 or 500 µM oxotremorine and then the enhancement of $K^+$-ERDA was assessed. Dopamine release was quantitated by HPLC coupled to electrochemical detection and expressed as pmoles/mg protein as determined by the Lowry procedure.

Figure 5:
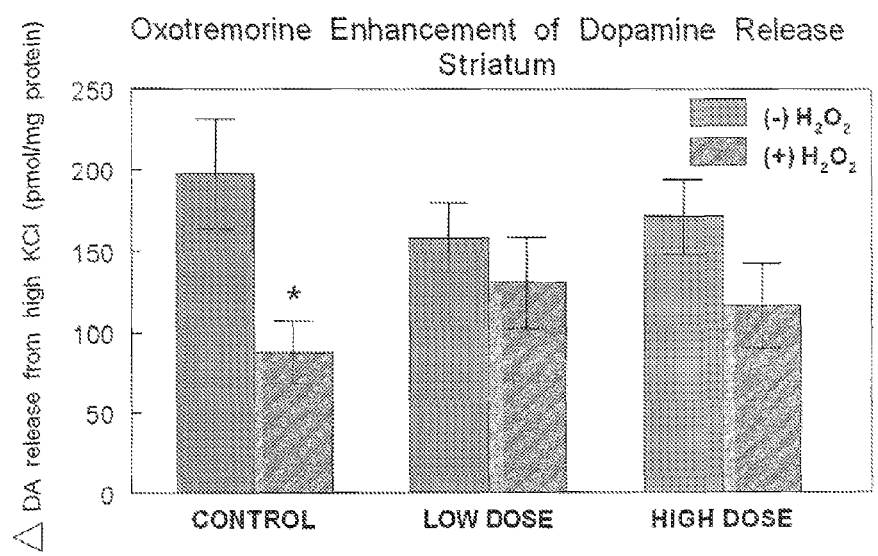
FIG. 5 is a graph of oxotremorine enhancement of dopamine release from striatal slices (change in pmol/mg protein) prepared from subjects maintained on the control, low dose pterostilbene (0.004%), and high dose pterostilbene (0.016%) diets, under basal levels (−$H_2O_2$) and under conditions of oxidative stress (+$H_2O_2$, 50 μM) treatment. The asterisk indicates a difference in dopamine release between non-$H_2O_2$-treated and $H_2O_2$-treated striatal slices for each diet group (*=$p<0.01$).

Dopamine release (oxotremorine-enhanced striatal $K^+$-ERDA) was significantly different among the groups, depending on the diet and $H_2O_2$ treatment [$F(5.58)=2.34$, p<0.05] (FIG. 5). Under basal conditions, there were no differences among the diet groups (p>0.05). However, dopamine release was significantly reduced in the $H_2O_2$-treated control diet group compared to the non-$H_2O_2$-treated control diet group (p<0.05), whereas no differences were seen following $H_2O_2$ treatment in subjects administered a therapeutic amount of either low or high dose pterostilbene.

While the invention has been described with reference to details of the illustrated embodiment, these details are not intended to limit the scope of the invention as defined in the appended claims. The embodiment of the invention in which exclusive property or privilege is claimed is defined as follows:

The invention claimed is:
1. A method for increasing the working memory of a subject, the method comprising administrating to a subject in need thereof an effective amount of isolated or purified pterostilbene, wherein the working memory for the subject is increased.

2. The method as recited in claim 1 wherein the effective amount of isolated or purified pterostilbene is about 10 mg of compound per kilogram of subject body weight.

3. The method of claim 1 wherein the effective amount of isolated or purified pterostilbene is an amount about 2.5 mg to about 10 mg of compound per kilogram of subject body weight.

* * * * *